United States Patent
McCallie, Jr. et al.

(10) Patent No.: US 7,953,608 B2
(45) Date of Patent: May 31, 2011

(54) SYSTEM AND METHOD FOR ORCHESTRATING CLINICAL COLLABORATION SESSIONS

(75) Inventors: David P. McCallie, Jr., Stilwell, KS (US); Christopher S. Finn, Liberty, MO (US); David J. O'Larte, Peculiar, MO (US); Steven S. Crooks, Gladstone, MO (US)

(73) Assignee: Cerner Innovation, Inc., Overland Park, KS (US)

( * ) Notice: Subject to any disclaimer, the term of this patent is extended or adjusted under 35 U.S.C. 154(b) by 1828 days.

(21) Appl. No.: 11/023,057

(22) Filed: Dec. 27, 2004

(65) Prior Publication Data
US 2006/0143043 A1    Jun. 29, 2006

(51) Int. Cl.
*G06Q 50/00* (2006.01)

(52) U.S. Cl. .................. 705/2; 709/7; 434/236; 434/238

(58) Field of Classification Search .................. 705/2, 3
See application file for complete search history.

(56) References Cited

U.S. PATENT DOCUMENTS
7,379,964 B1 * 5/2008 Buechler et al. .............. 709/203
* cited by examiner

*Primary Examiner* — R. D Rines
(74) *Attorney, Agent, or Firm* — Shook, Hardy & Bacon L.L.P.

(57) ABSTRACT

A system and associated methods for orchestrating a collaboration session are disclosed. One method involves orchestrating a collaboration session between a requesting clinician and another clinician where information is exchanged electronically. According to the method, requests for collaboration sessions are received by a computer system from the requesting clinician, with a given request related to a piece of patient-focused clinical data. Each request is analyzed to build a roster of potentially available clinicians for collaboration. A collaboration session is then facilitated between the requesting clinician and one or more of the potentially available clinicians on the roster.

28 Claims, 7 Drawing Sheets

FIG. 4

SYSTEM AND METHOD FOR ORCHESTRATING CLINICAL COLLABORATION SESSIONS

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

The present invention relates generally to the field of computer software. More particularly, the present invention relates to a computerized system and method for facilitating clinical collaboration sessions.

Modern health care delivery for a given patient involves an increasingly complex network of clinicians. These clinicians may include healthcare professionals, such as doctors, nurses, physical therapists, and others, as well as related staff members. Clinicians frequently generate a large amount of patient-related data, at least some of which are stored in the associated patient's electronic medical record (EMR) stored within a computerized clinical information system. These data may include (i) observations made by the clinicians and memorialized in the record, (ii) results of various tests the patient has undergone, or (iii) various documents (e.g., in the form of attached files) containing information related to the patient, as examples.

A clinician treating a given patient may want to know more about data within the patient's EMR or other record related to the patient. For instance, a primary care physician treating a patient for a particular ailment may want to ask a radiologist about a diagnosis made based on the results of an x-ray or MRI image for the patient. One way to accomplish this is to track down the author of the data, or a clinician of a certain level of expertise that could help in explaining and/or interpreting the data. These individuals, however, are often scattered throughout a health system or institution. In fact, "face-to-face" contact between and among treating clinicians is decreasing because electronic patient records may be stored on networked information systems (e.g., LANs, WANs) and accessed remotely by authorized users. There is not a strong necessity for clinicians to be physically located within the same building or even geographic area. Even if data authors are found, they may be occupied with other tasks that prevent them from having a discussion with the requesting clinician. Clinicians that have a certain specific medical expertise, or association with the data author, are likewise difficult to locate, and identifying their degree of relevance to the medical issue or data at hand may be impossible based only on the patient's record.

Clinicians are, therefore, desiring to more quickly and effectively locate and engage in collaboration with other individuals to aid in delivering health care services to a given patient. It is advantageous for clinicians requesting collaboration sessions to, at times, have additional contextual information regarding the patient or relevant data within a record. There is also a desire for collaboration to take place dynamically and with the exchange of data that may be embodied in various electronic forms, such as text, voice and graphical.

BRIEF SUMMARY OF THE INVENTION

The present invention generally provides a system and associated methods whereby a requesting clinician may develop a roster of potential collaborating clinicians and engage in a collaboration session with available clinicians on the roster. The collaboration session is conducted electronically.

One aspect of the present invention includes a method in a computer system for generating a roster of potentially available clinicians for a collaboration session with a requesting clinician. According to the method, requests for collaboration sessions are received by the computer system from the requesting clinician. Each request relates to a piece of patient-focused clinical data, such as a treating clinician's name or other information within a medical record. Requests are then analyzed to produce identities for the potentially available clinicians.

Another aspect of the present invention includes a method in a computer system for orchestrating a collaboration session between a requesting clinician and another clinician. According to the method, requests for collaboration sessions are received by the computer system from the requesting clinician, with a given request related to a piece of patient-focused clinical data. Each request is analyzed to build a roster of potentially available clinicians for collaboration. A collaboration session is then facilitated between the requesting clinician and one or more of the potentially available clinicians on the roster, where electronic information may be shared between the collaborating clinicians.

The invention of another aspect includes a computer system for orchestrating a collaboration session involving a requesting clinician and one or more potentially available clinicians. The computer system has a receiving component that receives a request from the requesting clinician for the collaboration session on a piece of patient-focused clinical data. The receiving component communicates the request to a roster generation component, which builds a roster comprising potentially available clinicians that are related to the piece of patient-focused clinical data. Once the roster is built, an interfacing component may be employed to facilitate the collaboration session between the requesting clinician and one or more potentially available clinicians on the roster.

BRIEF DESCRIPTION OF THE SEVERAL VIEWS OF THE DRAWING

In the accompanying drawings which form a part of the specification and are to be read in conjunction therewith and in which like reference numerals are used to indicate like elements in the various views:

FIG. 4 illustrates an example of an electronic medical record;

DETAILED DESCRIPTION OF THE INVENTION

The present invention provides a system and associated methods that allow for the generation of a roster of potentially available clinicians for a collaboration session with a requesting clinician, and then for facilitating such a collaboration session. This allows for a clinician to better locate others that may provide helpful medical information and/or context to patient-focused clinical data of a medical record. The collaboration session is conducted electronically, enabling the clinicians to be remotely located with respect to one another.

Figure 1:
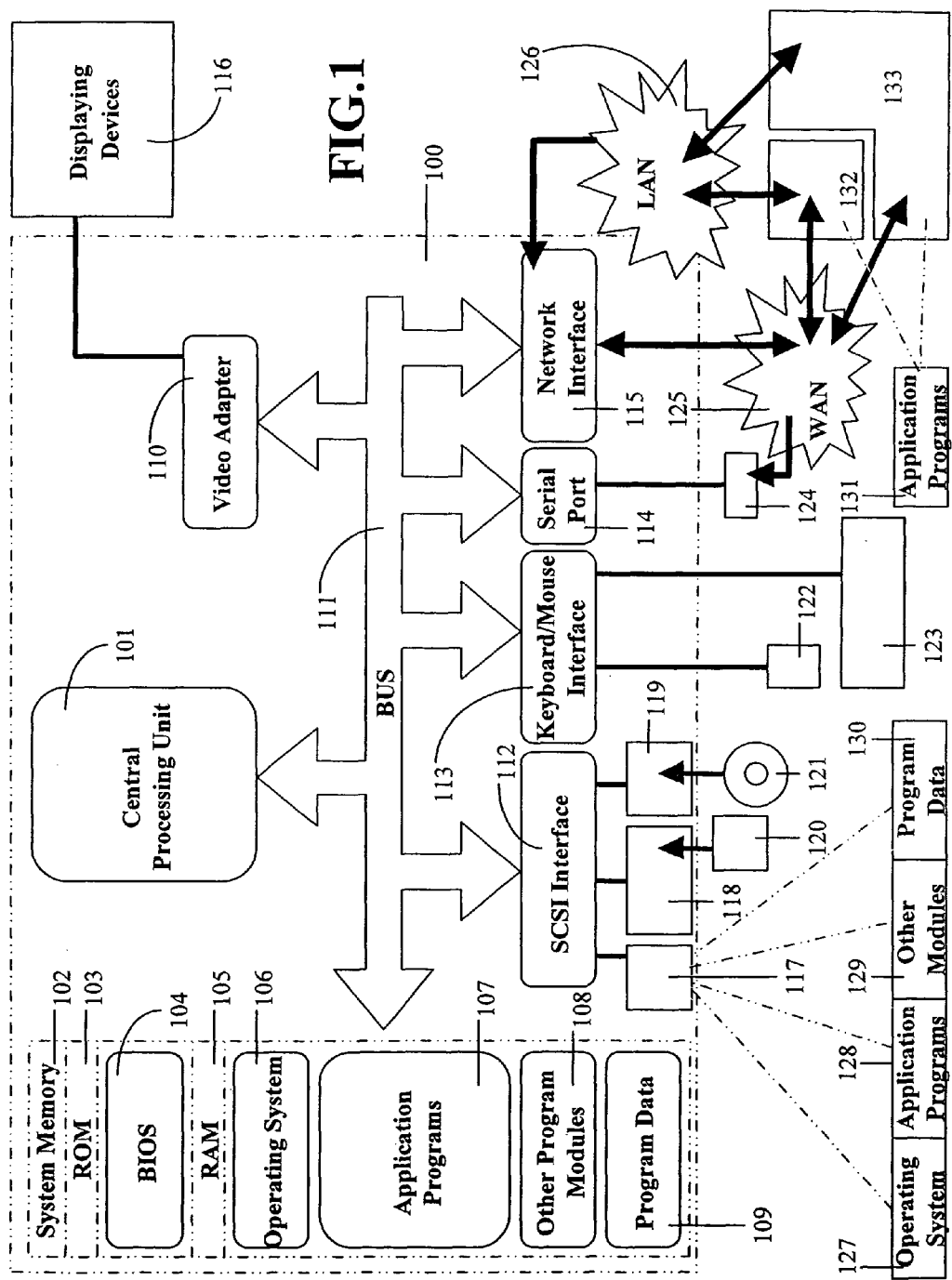
FIG. 1 is a block diagram of a computing system suitable for use in implementing the present invention.

FIG. 1 illustrates an example of a suitable computing system environment in which the invention may be implemented. The computing system environment is only one example of a suitable computing environment and is not intended to suggest any limitation as to the scope of use or functionality of the invention. Neither should the computing system environment be interpreted as having any dependency or requirement to any one or combination of components illustrated in the exemplary operating environment.

The present invention is operational with numerous other general purpose or special purpose computing system environments or configurations. Examples of well known computing systems, environments, and/or configurations that may be suitable for use with the invention include, but are not limited to, personal computers, server computers, hand-held or laptop devices, cellular telephones, portable wireless devices, multiprocessor systems, microprocessor-based systems, programmable consumer electronics, network PCs, minicomputers, mainframe computers, distributed computing environments that include any of the above systems or devices, and the like.

The present invention may be described in the general context of computer-executable instructions, such as program modules, being executed by a computer. Generally, program modules include routines, programs, objects, components, data structures, etc. that perform particular tasks or implement particular abstract data types. The invention may also be practiced in distributed computing environments where tasks are performed by remote processing devices that are linked through a communications network. In a distributed computing environment, program modules may be located in both local and remote computer storage media including memory storage devices.

With reference to FIG. 1, an exemplary system for implementing the invention includes a general purpose computing device in the form of a computer or computing system 100. It should be understood that the terms "computer" or "system" may be used interchangeably when referring to computing system 100. System 100 serves at least in part as a general medical information system. Components of system 100 include, but are not limited to, a processing unit 101, a system memory 102, and a system bus 111 that couples various system components including the system memory 102 to the processing unit 101. The system bus 111 may be any of several types of bus structures including a memory bus or memory controller, a peripheral bus and a local bus using any of a variety of bus architecture. By way of example, and not limitation, such architectures include Industry Standard Architecture (ISA) bus, Micro Channel Architecture (MCA) bus, Enhanced ISA (EISA) bus, Video Electronics Standard Association (VESA) local bus, and Peripheral Component Interconnect (PCI) bus also known as Mezzanine bus.

System 100 typically includes a variety of computer readable media. Computer readable media can be any available media that can be accessed by system 100 and includes both volatile and nonvolatile media, removable and nonremovable media. By way of example, and not limitation, computer readable media may comprise computer storage media and communication media. Computer storage media includes both volatile and nonvolatile, removable and nonremovable media implemented in any method or technology for storage of information such as computer readable instructions, data structures, program modules or other data. Computer storage media includes, but is mot limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by system 100. Communications media typically embodies computer readable instructions, data structures, program modules or other data in a modulated data signal such as a carrier wave or other transport mechanism and includes any information delivery media. The term "modulated data signal" means a signal that has on or more of its characteristics set or changed in such a manner as to encode information in the signal. By way of example, and not limitation, communication media includes wired media such as a wired network or direct wired connection, and wireless media such as acoustic, radio frequency (RF), infrared and other wireless media. Combinations of any of the above should also be included within the scope of computer readable media.

The system memory 102 includes computer storage media in the form of a volatile and/or nonvolatile memory such as read only memory (ROM) 103 and random access memory (RAM) 105. A basic input/output system (BIOS) 104, containing the basic routines that help to transfer information between elements within system 100, such as during start-up, s typically stored in ROM 103. RAM 105 typically contains data and/or program modules that are immediately accessible to and/or presently being operated on by processing unit 101. By way of example, and not limitation, FIG. 1 illustrates operating system 106, application programs 107, other program modules 108, and program data 109.

The system 100 may also include other removable/nonremovable, volatile/nonvolatile computer storage media. By way of example only, FIG. 1 illustrates a hard disk drive 117 that reads from or writes to nonremovable, nonvolatile magnetic media, a magnetic disk drive 118 that reads from or writes to removable, nonvolatile magnetic disk 120, and an optical disk drive 119 that reads from or writes to a removable, nonvolatile optical disk 121 such as a CD ROM or other optical media. Other removable/nonremovable, volatile/nonvolatile computer storage media that can be used in the exemplary operating environment include, but are not limited to, magnetic tape cassettes, flash memory cards, digital video disks, digital video tape, Bernoulli cartridges, solid state RAM, solid state ROM, and the like. The hard disk drive 117, magnetic disk drive 118 and optical disk drive 119 are typically connected to the system bus 111 by a Small Computer System Interface (SCSI) 112. Alternatively, the hard disk drive 117, magnetic disk drive 118 and optical disk drive 119 may be connected to the system bus 111 by a hard disk drive interface, a magnetic disk drive interface, and an optical drive interface, respectively.

The drives and their associated computer storage media discussed above and illustrated in FIG. 1, provide storage of computer readable instructions, data structures, program modules and other data for the system 100. In FIG. 1, for example, hard disk drive 117 is illustrated as storing operating system 127, application programs 128, other program modules 129, and program data 130. Note that these components can either be the same as or different from operating system 106, application programs 107, other program modules 108, and program data 109. A user may enter commands and information into the system 100 through input devices such as a keyboard 123 and pointing device 122, commonly referred to as a mouse, trackball or touch pad. Other input devices (not shown) may include a microphone, joystick, game pad, satellite dish, scanner, or the like. These and other input devices are often connected to the processing unit 101 through a user input interface 113 or a serial port interface 114 that is coupled to the system bus 111, but may be connected by other interface and bus structures, such as a parallel port, game port or a universal serial bus (USB). A monitor 116 or other type of display device is also connected to the system bus 111 via an interface, such as a video adapter 110. In addition to the monitor 116, computers may also include other peripheral output devices such as speakers and printers, which may be connected through an output peripheral interface.

The system 100 may operate in a networked environment using logical connections to one or more remote computers, such as a remote computer 133 and/or other communications, such as a communication device 132. The remote computer 133 may be a personal computer, a server, a router, a network PC, a peer device or other common network node, and typically includes many or all of the elements described above relative to the system 100, although only a memory storage device has been illustrated in FIG. 1. Remote computer 133 may, for example, be found at a variety of health system related locations, such as hospitals, other inpatient settings, pharmacies, a clinician's office, ambulatory settings, testing labs and a patient's home environment, though other locations may be chosen as well. The communication device 132 may be a mobile cellular phone, mobile text-pager or other portable communications device, and typically includes some of the elements described above relative to the system 100. The logical connections depicted in FIG. 1 include a local area network (LAN) 126 and a wide area network (WAN) 125, but may also include other networks. Such networking environments are commonplace in offices, enterprise-wide computer networks, intranets and the Internet.

When used in a LAN networking environment, the system 100 is connected to the LAN 126 through a networking interface or adapter 115. When used in a WAN networking environment, the system 100 typically includes a modem 124 or other means for establishing communications over the WAN 125, such as the Internet. The modem 124, which may be internal or external, may be connected to the system bus 111 via the serial port interface 114 or other appropriate mechanism. In a networked environment, program modules depicted relative to the system 100, or portions thereof, may be stored in the remote storage device. By way of example, and not limitation, FIG. 1 illustrates remote application programs 131 as residing on memory devices 132 and 133. It will be appreciated that the network connections shown are exemplary and other means of establishing a communications link between the computers and/or portable communication devices may be used.

Although many other internal components of the system 100 are not shown, those of ordinary skill in the art will appreciate that such components and the interconnection are well known. Accordingly, additional details concerning the internal construction of the computer 20 need not be disclosed in connection with the present invention.

Those skilled in the art will understand that program modules such as the operating system 106 and 127, application programs 107 and 128, and program data 109 and 130 are provided to the system 100 via one of its memory storage devices, which may include ROM 103, RAM 105, hard disk drive 117, magnetic disk drive 118 or optical disk drive 119. Preferably, the hard disk drive 117 is used to store program data 130 and 109, application programs 107 and 128, and operating system 106 and 127.

When the system 100 is turned on or reset, the BIOS 104, which is stored in the ROM 103 instructs the processing unit 101 to load the operating system from the hard disk drive 117 into the RAM 105. Once the operating system 127 is loaded in RAM 105, the processing unit 101 executes the operating system code and causes the visual elements associated with the user interface of the operating system 127 to be displayed on the monitor 116. When an application program 107 and 128 is opened by a user or waken up by an inbound request for collaboration, the program code and relevant data are read from the hard disk drive 117 and stored in RAM 105.

Figure 2:
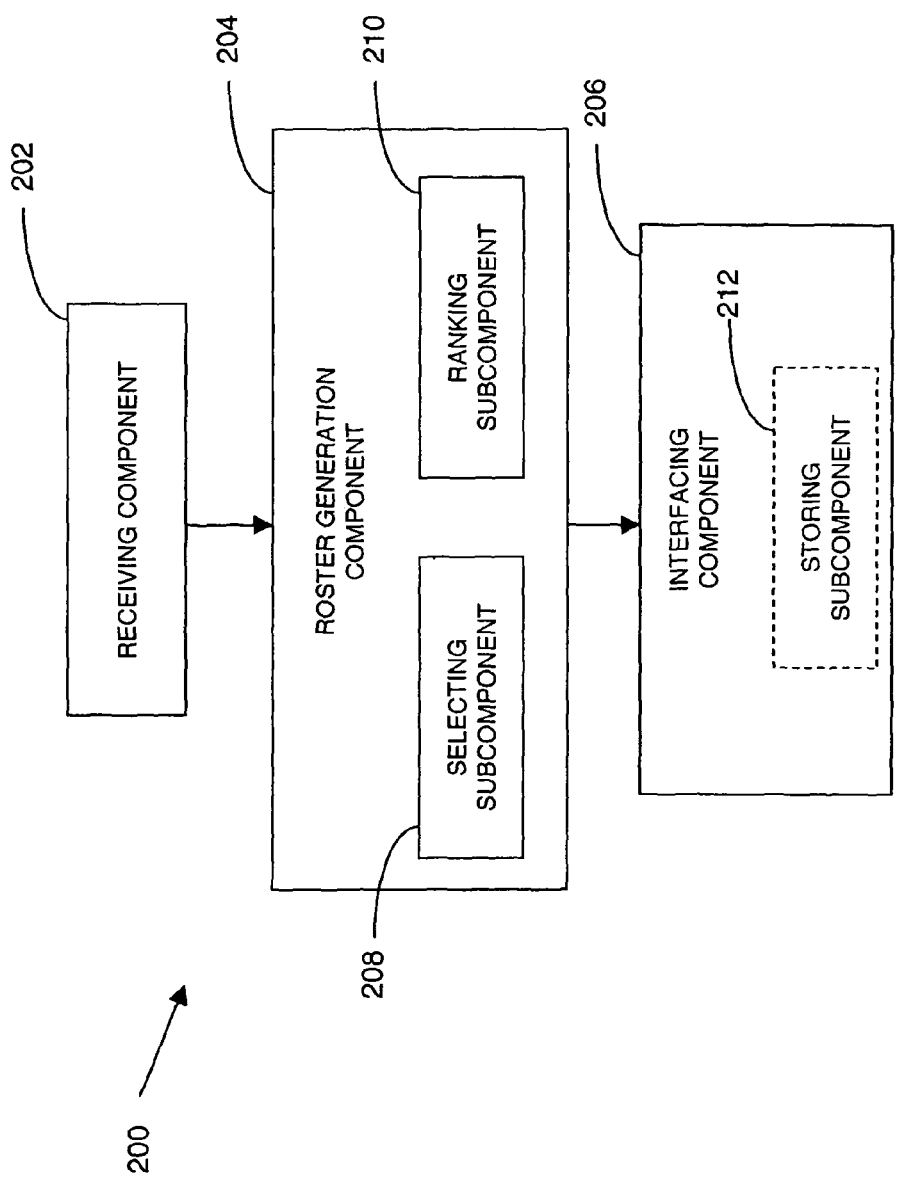
FIG. 2 is a flow diagram illustrating a sequential flow through high-level components.

The sequential flow of activity through a set of general component modules 200, functioning within the system 100, can be viewed with reference to FIG. 2. Various terminology discussed with respect to the present invention may have particular meaning as described below. For instance, the term "clinician" includes, but is not limited to, a treating physician, specialists such as surgeons, radiologists and cardiologists, emergency medical technicians, physician's assistants, nurse practitioners, nurses, physical therapists, pharmacists, dieticians, microbiologists, and the like, and aides or assistants thereto. The term "patient" refers to a person that is receiving or has received health-care-related services in any location in a medical environment (e.g., hospitals or other inpatient or outpatient settings, a clinician's office, ambulatory settings, testing labs, patient's home environment, or in any other setting). The set of general component modules 200 interact with various types of medical records that contain information about patients. As an example, these medical records may take the form of an electronic medical record (EMR) for a particular patient. The electronic medical record is typically designed to contain various types of information about an individual patient, such as: observed conditions of the patient (e.g., physiological conditions such as blood pressure, oxygen saturation levels in blood, or other "vital signs"); medications taken; current immunizations; food and drug allergies; diagnoses of various clinicians; listing of clinician names that are currently providing or that have provided care to the patient; and may include, directly in the EMR or attached thereto, other files containing various information/data, such as image data (e.g., X-ray, MRI image, skin or tissue photos), voice data (e.g., .wav file or other audio formatted recording of clinician providing patient-related information), or other textual information. The information in an EMR or other medical record as described herein may be referred to generally as patient-focused clinical data. However, it should be understood that the term "medical record", or "electronic medical record" in particular, should not be interpreted to be limited to any type of computer-readable format or record, but includes any electronically-stored data structure containing information relative to at least one specific patient and from which information may be viewed and/or extracted by the system of the present invention.

The general component modules 200 include, in one embodiment, a receiving component 202, a roster generation component 204 and an interfacing component 206. Methods for facilitating collaboration sessions of the present invention generally involve actions that flow from the receiving component 202, to the roster generation component 204, and on to the interfacing component 206. The receiving component 202 may be configured to receive a request for the initiation of a collaboration session between a requesting clinician and one or more other clinicians that may potentially be available to collaborate. Such a collaboration request relates to a piece of the patient-focused clinical data (also referred to as the "context") that resides, for example, in a medical record, such the particular patient's EMR. Selection of the context causes the request for collaboration session initiation to be generated. Based on the context related to, or contained within, the request, the roster generation component 204 begins the building of a roster of specific potentially available clinicians using a selecting subcomponent 208 and a ranking subcomponent 210. Certain input from the requesting clinician and analysis by the roster generation component 204 and subcomponents thereof may be used to configure and arrange the roster of potentially available clinicians for collaboration. Once the roster is complete, the interfacing component 206 sends invitations for a collaboration session for those entities on the roster, and subsequently receives replies from entities interested in joining the session. The interfacing component may also negotiate the capabilities of all collaborating entities, including the requesting clinician, and determines which mode of electronic communication is feasible and/or preferred for the session.

Figure 3:
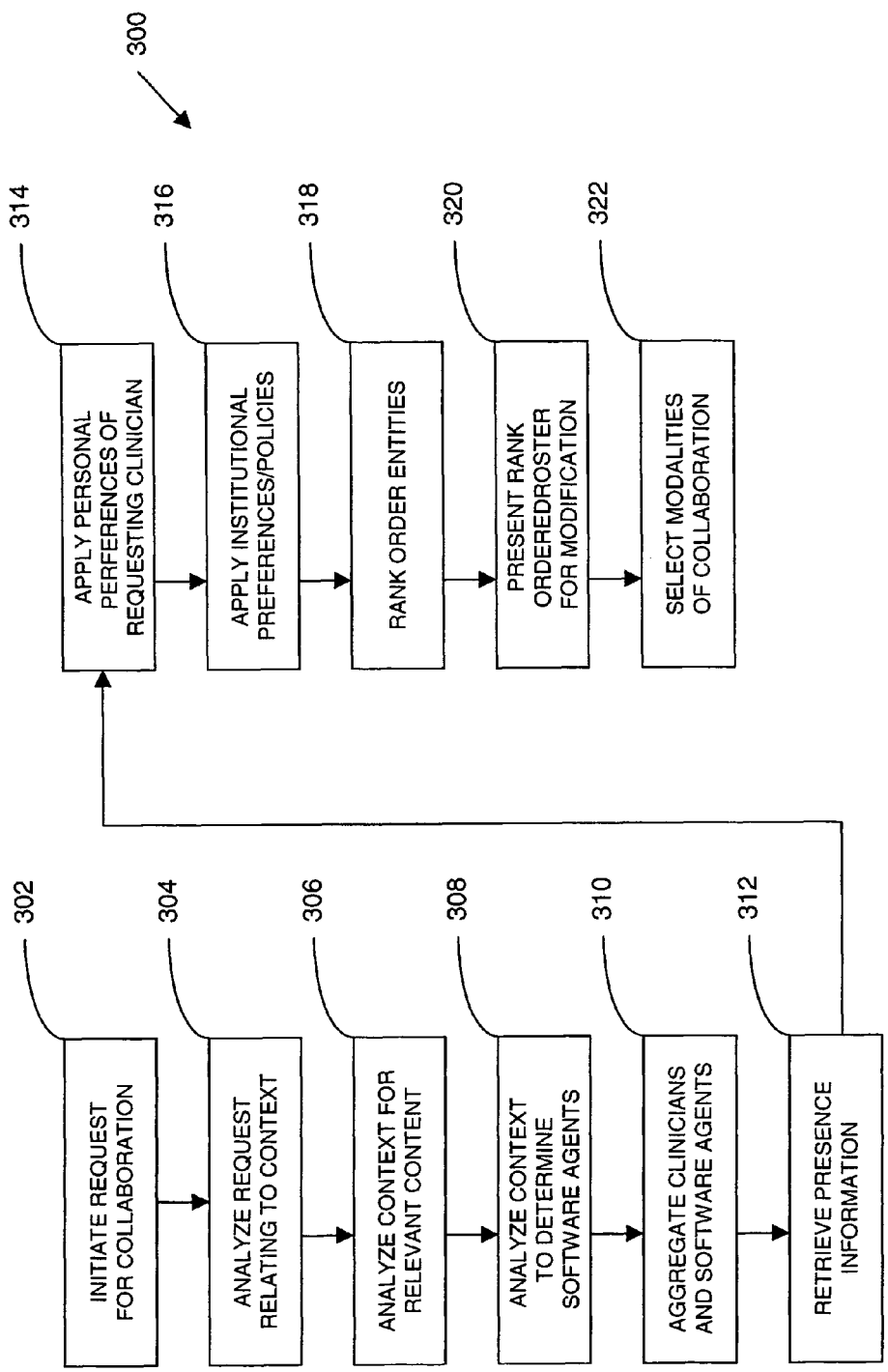
FIG. 3 is a flow diagram of one method for roster generation.

One method 300 of roster generation concerning potentially available clinicians for a collaboration session is presented in FIG. 3. Reference will also be made to the general component modules 200 of FIG. 2. The method 300 is capable of implementation with a particular patient's EMR, such as a medical record 400 shown in FIG. 4, which will be described and referenced along with the discussion of FIG. 3.

Figure 4:
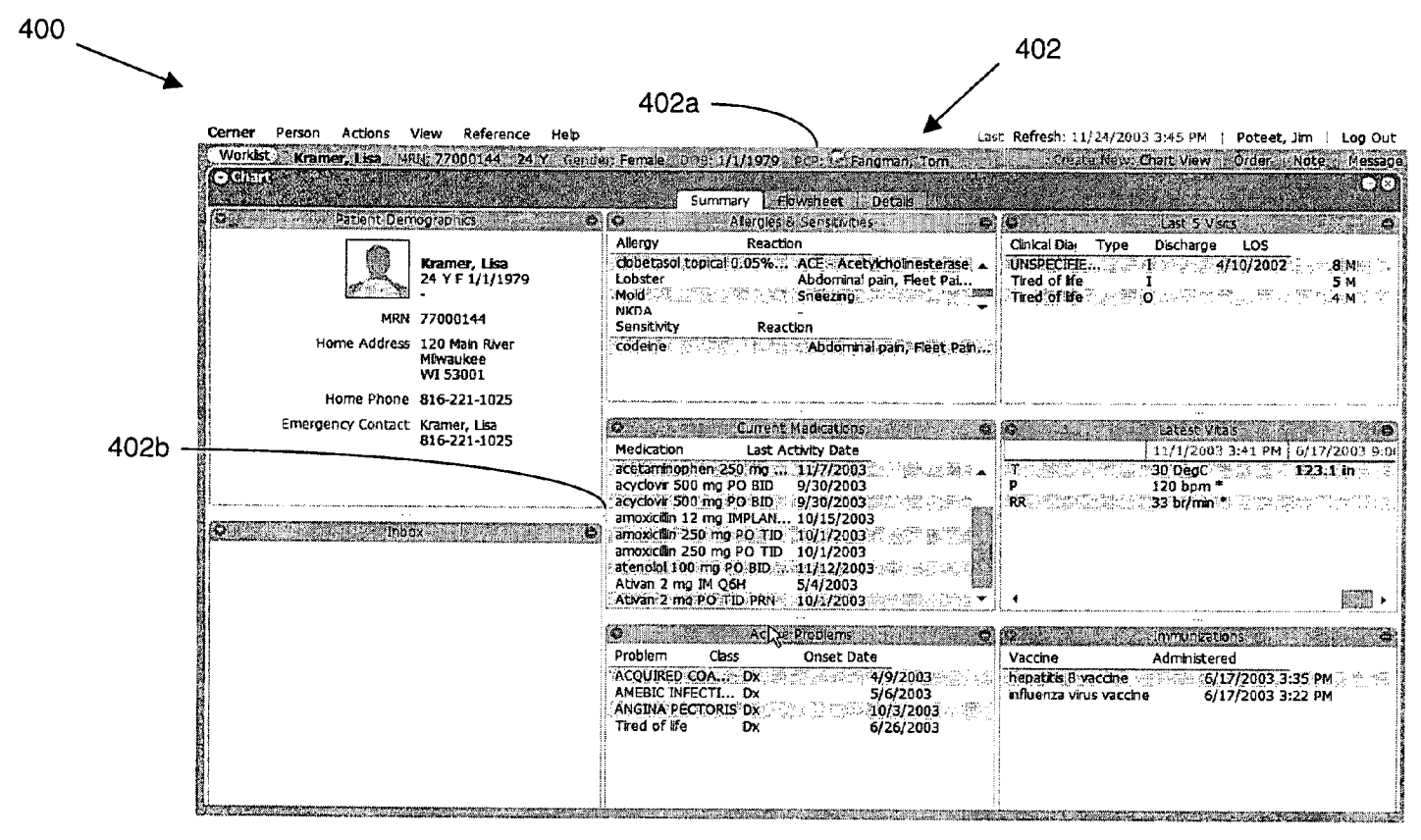

A requesting clinician will first initiate a request for a collaboration session upon a piece of patient-focused clinical data (i.e., the "context"), in step 302. An example of this context is shown in FIG. 4 and generally designated 402. The context 402 may be generally classified into one of two categories. In either category, the context is preferably hyperlinked for negotiating a certain access protocol to reach the roster building capabilities of the roster generation component 204. The hyperlinked context is selectable with any input device (e.g., a mouse). The first category of context 402a may include individual caregivers or clinicians listed in the medical record 400; in other words, "record related clinicians." In the example shown, the Primary Care Physician ("PCP") is "Tom Fangman." By selecting the Primary Care Physician as the record related clinician, other clinicians having some connection with the Physician may be brought to the attention of the requesting clinician, as will be explained below. Alternatively, the second category of context 402b may include certain types of information or data other than clinicians. For example, certain information in medical record 400 may be eligible as something about which to spur a collaboration request, and may be so identified with certain visual cues, such as a "Collaborate About" icon next to the context 402b. Context 402b can include, but is not limited to, information such as vital signs, current medications, allergies, clinical diagnoses, and problems articulated by the patient. The receiving component 202 receives these selections as requests to build a roster, and invokes the roster generation component 204 to conduct a collaboration session.

The method continues at step 304, where the roster generation component 204 analyzes the received selection relating to one of the particular pieces of context 402a or 402b to identify clinicians having some connection with, or relevancy to, the chosen context. A list of all the clinicians in a given institution that may be contacted may be maintained, for example, in a searchable database of the system 100 located on one or more of the storage devices 117, 118, 119, or at another location in a medical information system.

In the case of the context 402a being a clinician (i.e., a record related clinician), other categories of relevant clinicians may include, but are not limited to: (i) clinicians associated with the record related clinician, such as other clinicians in their practice group or organization (e.g., a primary care physician or nurse); (ii) clinicians associated with the record related clinician and the requesting clinician, which may be referred to as "associates-in-common" (e.g., clinicians in the same practice group or organization as the record-associated and requesting clinician, or clinicians frequently utilized by both clinicians); (iii) clinicians that share the same role as the record related clinician, such as in the example of medical record 400, Primary Care Physicians in addition to "Tom Fangman"; or (iv) clinicians in a "web of care" with the patient whose medical record 400 contains the context 402a. The concept of web of care relates to a quantitative measurement of the relationship between the clinician and patient. This relationship may take into account a number of factors, including the quality, nature, and frequency of contact or care given by the clinician for the patient, as is explained in U.S. patent application Ser. No. 10/860,458, filed Jun. 4, 2004 and entitled "SYSTEM AND METHOD FOR CREATING A VISUALIZATION INDICATING RELATIONSHIPS AND RELEVANCE TO AN ENTITY," the teachings of which are incorporated herein by reference.

Alternatively, when the initiation of a request for a collaboration session is through context 402b as data other than clinician names, various relevant clinicians may include, but are not limited to: (i) those clinicians that are authors of such context 402b or initiated an activity to derive the context 402b (e.g., ordered an X-ray attached with the medical record 400); or clinicians related to the authors/initiators of the context 402b, where the relationship involves one of the clinician associations recited above with respect to the context 402a being a clinician.

The activity in step 304 of the method is performing a merging of various social networks within an institution to find an initial set of potential clinician collaborators that is at least partially based on the perceived intent of the requesting clinician. Thus, the method 300 is working towards finding the individuals that will have the most relevant information about the patient-focused clinical data.

After an initial set of potential clinician collaborators relevant to the context is established, and in the case of the patient-focused clinical data being other than a clinician name, i.e., context 402b, the roster generation component 204 may analyze the context 402b for relevant content to share with the requesting clinician in conjunction with the context 402b, in step 306.

For instance, this method step may optionally involve selection of a relevance perspective corresponding to the context 402b. The selected relevance perspective may be used in a clinical relevance scoring algorithm to rank order the roster of potentially available clinicians, as will be more fully explained below. In a sense, the relevance perspective defines a mathematical function modeling a particular health care treatment scenario for a given patient.

One particular example of a relevance perspective involves identifying the most relevant clinical decision maker for a patient. In this illustration, an applicable mathematical function places a higher value on, for example, the number of medication orders or invasiveness of the procedures undertaken on the patient. Another example of a relevance perspective involves identifying the clinician who, in a sense, best knows the patient's current care plan. This perspective places a higher value on the number of touches rather than the type of touch. In any case, the relevance perspective may either be a default selected by the roster generation component 204 for a particular context 402b, or may also selected by the requesting clinician from a predefined set of relevance perspectives stored with system 100.

Alternatively, the analysis undertaken by the roster generation component 204 in step 306 may be conducted without regard to any relevance perspective. For instance, if the requesting clinician wants to collaborate about a diagnosis or medication listed in a given patient's medical record 400, it may be desirable for the requesting clinician and/or any collaborating clinician to select other patient related data (e.g., demographics, past diagnoses) for display or quick reference during a collaboration session. Such additional patient related data may, as an example, be accessed through a hyperlinked uniform resource locator (URL) to allow navigation through the medical information system to a proper file or record location, in accordance with known security and preference privileges, as those of skill in the art will appreciate. This additional patient related data will allow clinicians participating in the collaboration to put into the proper perspective patient issues that become part of the collaboration session.

The method 300 may also include, in step 308, analyzing the patient-focused clinical data or context 402 to determine if any software agents should be invited to the collaboration session. Software agents generally include executable software knowledge program modules contained within the system 100 that monitor and give guidance or other information based on the event flow during a collaboration session. The roster generation component 204 checks an existing mapping of the context 402 against software agents to determine which software agents may be appropriate for a collaboration session. This mapping may be pre-established in a medical information system (e.g., within a database thereof) based on the usefulness of information provided by the software agents in various situations. One example of a software agent is a question-answer engine that works on-demand for collaboration participants, retrieving information from a patient's EMR or from various databases holding medical information (e.g., the MULTUM database containing drug-drug interactions offered by Cerner Multum, Inc.), and commanding various medical devices to perform a task (e.g., take a blood pressure reading). The software agent may work by using natural language processing to understand requests logged by any collaborating clinician, whether entered into the system 100 by text, voice recognition or other means. Other actions may be taken by software agents to provide useful information in a collaboration environment, as those of skill in the art will appreciate. As another example, if the initial set of potential clinician collaborators include clinicians of a certain area of practice or specialty, for instance, oncology, then the software agent may provide information such as the definitions of relevant terminology within the specialty field, and may link such information with other information already being presented to the requesting collaborator and potential collaborators relating to the patient-focused clinical data.

There may be certain situations, however, where software agents may not be invoked even if available. If the processing burden placed on the medical information system by the software agent exceeds a given threshold, or if the particular user interfaces of electronic devices or computers used by the requesting collaborator and potential collaborators cannot display a certain type of content, then software agents may not be invoked at all (e.g., video data on a device displaying text only).

At this point in the method 300, the roster generation component 204 aggregates the initial set of potentially available clinicians from the previous method steps, and any software agents, into a preliminary roster, in step 310. Thus, at this point, the entities on the collaboration roster may include both human clinicians as collaborators and executable program modules.

Then, in step 312, the roster generation component 204 retrieves presence information for the potentially available clinicians on the roster. Such presence information may indicate contact-type information, such as the clinician's current location, online/offline status, availability, and/or collaboration device capabilities (e.g., for communications device 132 or remote computer 133). For instance, a signal requesting a response may be generated and transmitted by system 100 to the electronic devices associated with each clinician on the roster. The presence information on the roster may be updated in real-time and displayed as part of the roster so that the requesting clinician is informed of which potential clinician collaborators are, in fact, available for a collaboration session. During step 312, the component 204 is continuously acquiring, updating, and displaying availability information on the roster. Additionally, the presence information may be displayed in a variety of formats. For example, the color of an individual's name may represent the presence status of that individual. The color red may indicate that the individual is unavailable, yellow may indicate that the individual is busy, and green may indicate that the individual is available for collaboration. Other schemes may obviously be implemented, including other visual or audible cues indicating clinician availability.

A selecting subcomponent 208 of the roster generation component 204 may be used to apply personal preferences of the requesting clinician, as well as institutional preferences and policies, to the roster. This ensures that the roster of potentially available clinicians fully includes all persons that may be helpful and necessary to a collaboration session.

Specifically, in step 314, the selecting subcomponent 208 may apply personal preferences of the requesting clinician to the roster to allow for pre-selection of favorite or preferred collaborators to be included on the roster. These personal preferences may be clinicians with which the requesting clinician frequently collaborates, or software agents that the requesting clinician requires to monitor the collaboration session, as examples. As an illustration, a primary care physician may frequently want to include a particular nurse practitioner in all collaboration sessions conducted by the physician to ensure the best possible communication of relevant issues related to the care of a particular patient discussed in a collaboration session. As another example, a podiatrist as a requesting clinician may require a software agent configured to inject surgical diagrams into a collaboration session where the viewing of video images is possible. As will be understood, other examples may also be envisioned for this method step. These personal preferences are stored within the medical information system and may be edited and updated as desired by the requesting clinician.

The selecting subcomponent 208 may also take into account preferences and policies of an institution with which the requesting clinician and/or the potentially available clinicians are associated with in their respective medical practices, in step 316. The roster generation component 204 manages these preferences, which may include certain clinicians, role groups (e.g., a set of cardiologists), software agents, and the like, and ensures that these representative members of these preferential groups are present on the roster for the collaboration session if possible. The intent is that if an institution develops evidence that certain software agents or consultation patterns produce better outcomes in collaborative exchanges, the medical information system will support this by requiring the inclusion of the appropriate entities (i.e., human collaborators and software agents). Another situation that may necessitate the implementation of institution preferences and policies is when a requesting user is not a fullytrained practicing clinician, such as a student or intern in a health profession. As one example, the institution may require certain supervising clinicians be on the collaboration roster when the requesting user is a student nurse or an intern to evaluate or monitor the collaboration.

Once this stage of the method 300 has been reached, the roster now contains all of the entities that may potentially be part of a specific collaboration session. In step 318, a ranking subcomponent 210 of the roster generation component 204 is invoked to rank order entities using a clinical relevance scoring algorithm. This step may take into account the relevance perspective of step 304 and any previous rank ordering of potentially available clinicians.

Figure 5:
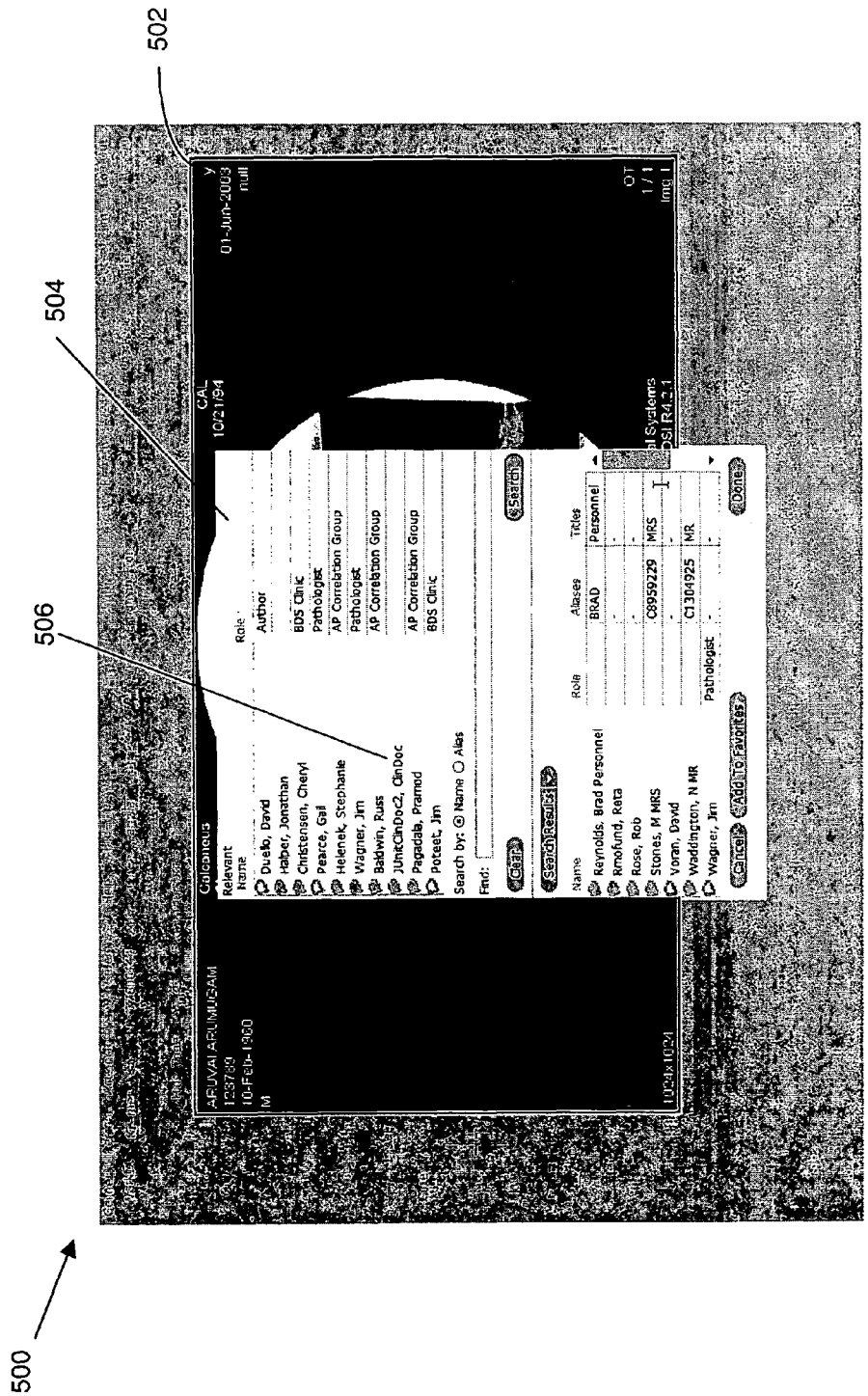
FIG. 5 illustrates one example of person-focused clinical data and a roster.

The ranking subcomponent 210 preferably uses the clinical relevance scoring algorithm to take into account the degree of clinical relevance between the entities on the roster and the piece of person-focused clinical data or context 402 that was selected by the requesting clinician in step 302. FIG. 5 shows one exemplary graphical interface 500 presenting a radiological image 502 selected as the context 402b in step 302, and a roster 504 of clinicians that have some relevancy to the context (or were otherwise selected by the requesting clinician and/or associated institution). Software agents may also be present on the roster 504, though not shown in FIG. 5. Various information about the clinicians may be provided, as more fully explained in previous steps of the method 300.

The clinical relevance scoring algorithm identifies the most relevant entities for this piece of context 402 and conducts roster ranking based on those results. Accordingly, the scoring algorithm may be implemented by a mathematical function that ranks, for the example roster 504 shown in FIG. 5, the author of the radiological image 502 first, followed by clinicians on the roster that have looked at the image for the particular patient, other clinicians that have not looked at that particular image but have a certain expertise in understanding radiological images in general (i.e., a radiologist), and lastly, other clinicians that have cared for the particular patient. The mathematical function for this scoring algorithm places a higher ranking value for individuals on the roster that have come in contact the most with the particular patient.

Generally, the clinical relevance scoring algorithm applies a mathematical function against data collected about particular activity types, including frequency of such activities, in order to rank the collaborators on the roster. The mathematical function may be a simple linear function or a more complex function applied to the activity data. In another illustration, the mathematical function for this scoring algorithm may rank the potentially available clinicians on the roster according to employment relationships with the requesting clinician. This may include clinicians on the roster that are in the same practice/role group as the requesting clinician, such as cardiologists, or that have been on the same medical team as the requesting clinician.

Continuing with step 320, the system 100 presents the rank ordered and complete roster of potentially available collaborating entities (i.e., clinicians and software agents) to the requesting clinician for modification thereof. The display of the complete roster may be in tabular form, for example, and presents the collaborator roster as arranged by the clinical relevance scoring algorithm or other rank order schemes. Additionally, the roster may contain a display of real-time presence information for each clinician shown. The requesting clinician can input selections of specific clinicians and software agents that the requester wishes to invite for a collaboration session such as by selecting boxes located next to the name of each potential collaborator. Certain boxes may already be checked or pre-selected based on the requesting clinician's stored preferences and the institution's stored preferences and policies, as described previously for steps 314 and 316. The roster of collaborators may be modified by selecting or de-selecting the entities on the complete roster. Optionally, the system 100 may allow the requesting clinician launch a person-to-person ad-hoc collaboration session with one of the clinicians on the roster whose presence information indicates that that individual is available for collaboration. Such an ad-hoc collaboration may be initiated by, for example, selecting an icon next to the clinician's name, or by clicking on the name itself.

Preferred modalities of collaboration may optionally be selected by the requesting clinician in step 322. These modalities refer to types of communications used in computing systems and other electronic devices. Examples of these modalities include, but are not limited to, text messaging, voice over internet protocol (IP), video, shared whiteboard or other real-time communicative collaboration capabilities, as those of skill in the art will appreciate. The requesting clinician may select one or more of the collaboration modalities, and information relating to these selected modalities may be transmitted as part of the entity invitation process, as will be more fully explained below. Additionally, based on the particular type of communication or computing device to be used by the requesting clinician for the collaboration session, the system 100 may automatically identify the capabilities of the device and preclude certain modalities of collaboration from being presented as an option for the clinician. Still further, if the particular device used by the requesting clinician is only capable of one modality of collaboration (e.g., a pager capable only of text messaging), then step 322 may be skipped.

Figure 6:
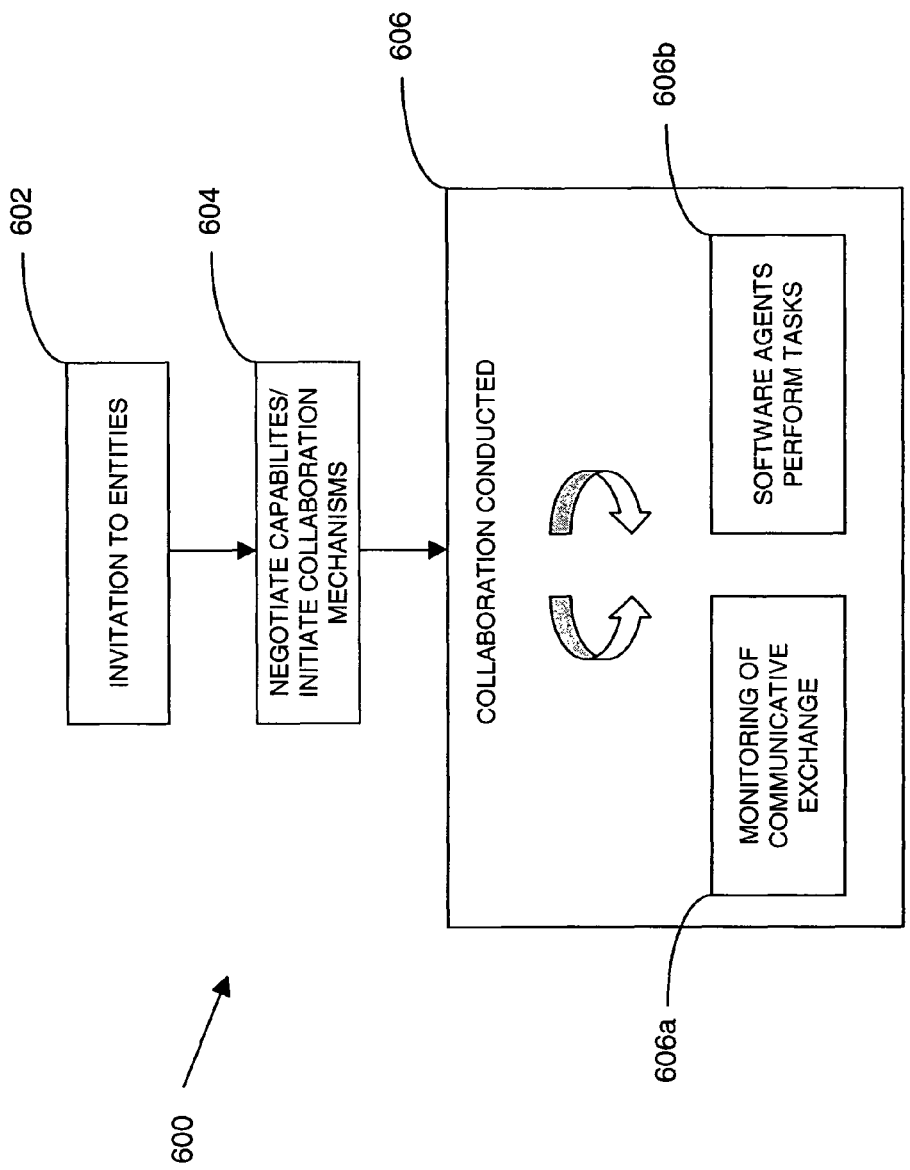
FIG. 6 is a flow diagram illustrating a method for facilitating a collaboration session.

At this point, roster generation is complete and the requesting clinician is ready to engage in a collaboration session with at least one of the potentially available clinicians and software agents on the roster. One method 600 for facilitating a collaboration session is set forth in FIG. 6 and with continued reference to the general component modules 200 of the system 100 shown in FIG. 2. In accordance with method 600, the interfacing component 206 receives the completed roster of entities for a collaboration session, and manages the collaborative exchange of information between the requesting clinician and entities that ultimately participate in the session.

The interfacing component 206, in step 602, and in view of selections made by the requesting clinician on the roster, invites the selected and potentially available clinicians and software agents (the entities) on the roster to participate in a collaboration session. Invitations to collaborate are sent to the entities along with information related to the desired/preferred collaboration modalities of the requesting clinician. In addition, the person-focused clinical data, or context, about which the requesting clinician wishes to collaborate may also be sent as part of the invitation. The clinical context data may optionally be presented as a hyperlinked uniform resource locator that the invited roster entities can invoke to begin a real-time collaboration session with the requesting clinician.

Thereafter, in step 604, interfacing component 206 negotiates the capabilities of the responding entities and initiates the appropriate collaboration mechanisms. The requesting clinician, the potentially available clinicians and software agents may be referred to collectively as "collaborators" when invited to, or currently participating in, a collaborative exchange of information within a collaboration session.

As a first action in step 604, the system, through interfacing component 206, receives replies from the invited collaborators along with the capabilities (i.e., modalities of collaboration) they support. For instance, an invited collaborator may respond by accepting the invitation and indicating that he/she is capable of collaborating through voice communication only. One example of a health care delivery situation where this could apply is with a surgeon presently occupied with a surgical procedure in an operating room. As to outside requesting clinicians seeking to collaborate with the surgeon, it may be most appropriate for the surgeon to provide speaking comments captured by a portable device or computer, but not for them to type any text or view any video images. Alternatively, the surgeon or other invited collaborators may respond by rejecting the invitation or may not respond to the invitation at all. These responses are noted by the component 206. The invitations for which no responses have been received may be left as open requests for collaboration or may be rescinded by the system or timed-out based on preferences of the system.

A number of additional rules may control the responding entities that are allowed to participate in the collaboration session. In one example, collaborative exchanges within the session may be conducted between the requesting clinician and one other clinician, although software agents may simultaneously participate as well. By limiting the session to two clinicians, the requesting clinician avoids information overflow in the exchange and is able to candidly evaluate the information gleaned from the other party without interference or interruption by other clinicians. At the same time, it may be desirable in certain circumstances for a given collaborative session to involve the requesting clinician and multiple other clinicians so that specific questions can be answered quickly by those who possess the best knowledge. The strength of medical opinions (e.g., diagnostic opinions) can also be verified more easily and thoroughly by multiple collaborating entities. As another rule, for invitations to role-groups, such as the "first available cardiologist" or "resident on call", the system is able to rescind all other invitations to that role group when any one of the clinician members accepts. This may be done by sending a notice to the other members in the role group that the invitation has been rescinded and disabling their ability to enter the collaboration session.

A second action of step 604 is, for the invited collaborators who have accepted the invitation, the interfacing component 206 establishing the appropriate connections necessary to initiate the collaboration session. Once the system confirms that such connections are established, in step 606, the collaboration session begins using the agreed-upon modalities. During the collaboration session, the requesting clinician may share some or all of the current pieces of patient-focused clinical data (e.g., context 402) and any other relevant content with the other collaborators. This may be done by sharing a URL for independent browsing of the record, with each collaborator having their own security and preferences applied, or by other sharing schemes. In one illustration, a requesting clinician may be currently looking at a clinical flow sheet contained in an electronic medical record, and desire that other collaborators look at the same sheet concurrently. The requesting clinician is able to send the URL for that flow sheet to the other collaborators so that each collaborator can browse to the correct location and filter it through their own security and preferences for independent browsing. Additionally, this may be done through an application sharing mode involving co-browsing.

Typically, collaboration in step 606 requires at least one human collaborator, such as a clinician; however, if a software agent has sufficient functionality, the agent may provide relevant information to the requesting clinician based on the context 402 without any human collaborators present.

Figure 7:
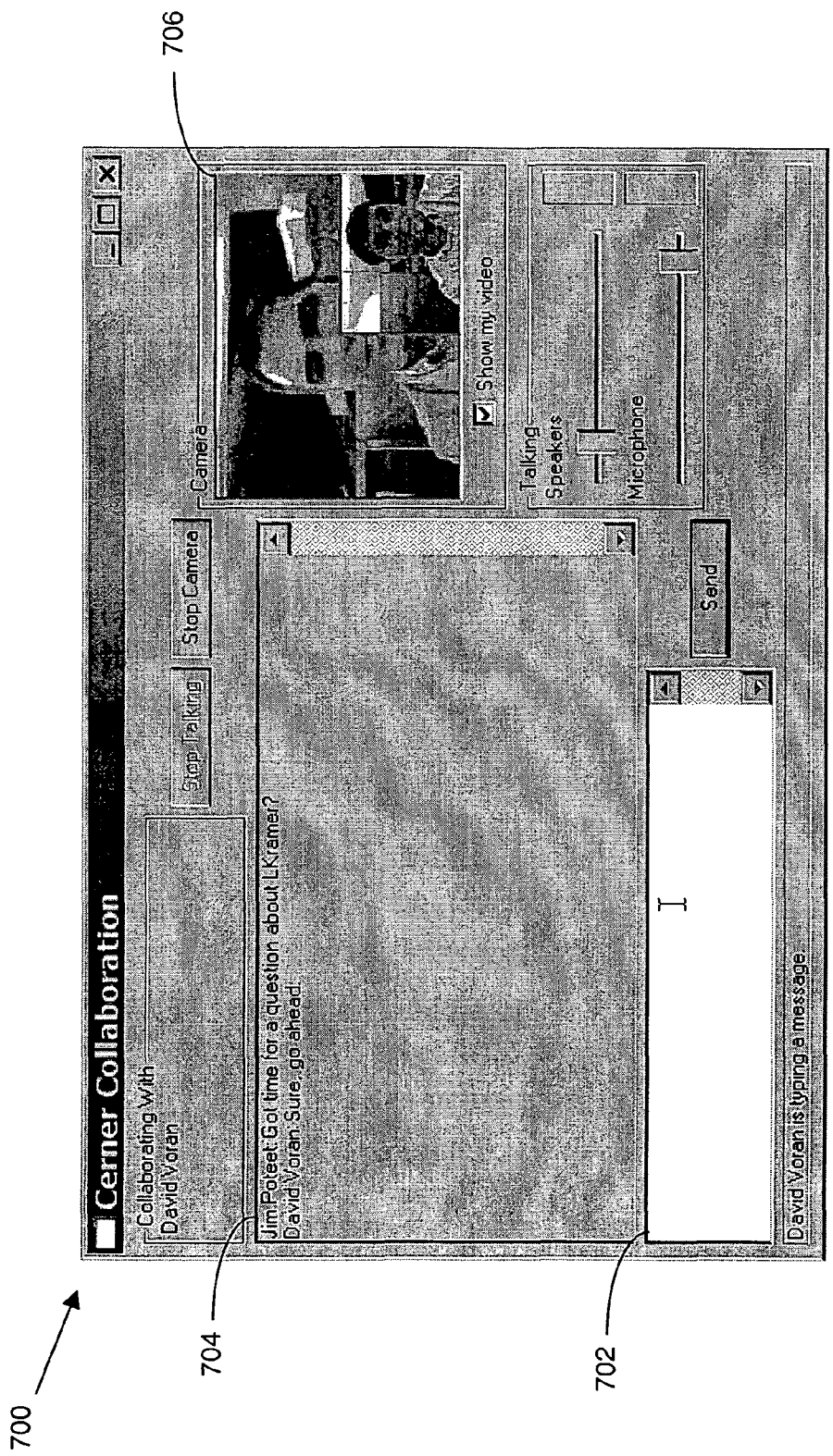
FIG. 7 is an exemplary graphical interface of a collaboration session.

One exemplary graphical interface 700 is provided in FIG. 7, and shows a collaboration session utilizing text message and video modalities for information exchange. Each collaborator can input text in text box 702 and view the exchange of textual information in display area 704. Additionally, the collaborators can see each other in the camera display area 706. Settings for the collaboration session are also configurable so that camera video images, or text messages (i.e., "talking") may be selectably activated or de-activated during the collaboration session by each collaborator.

Collaboration session activity in step 606 may involve parallel activities of specific software agents that were present on the collaboration roster generated. As a first parallel activity 606a within the collaboration session facilitated by the interfacing component 206, software agents monitor the communicative exchange between clinicians in the collaboration session for specific triggering events of interest. If such a triggering event is realized, a second parallel activity 606b is invoked where the software agent may perform one of a range of clinically relevant tasks. Illustrations of triggering events of interest may include a spoken word, a typed phrase, a call to the agent by name, user actions such as the sharing a newly created piece of patient-focused clinical data, or other type of event. As an example, during a collaboration session, the requesting clinician may call for a software agent called "OrderBot" to order a specific medication, in this case Acetaminophen 375 mg. OrderBot will then take action to order the prescribed medication for that particular patient. Another example may be a natural language processing agent that is aware of medical terminology that highlights words in text messages or voice transcripts, hyper linking them to their definitions or to related clinical actions from an evidence-based medicine standpoint. Still further, another example of a triggering event response may be software agents that act as question-answer systems on demand from collaborators, or agents that passively monitor the collaboration session and build annotated and conceptually abstracted transcripts. All of these software agents are capable of injecting the results into the events stream of the collaboration session.

The general component module 200 may additionally include a storing component 212 for storage any transcript or log of events and data streams built by the software agent or other system component during the collaboration session. Each transcript may be stored within the given patient's electronic medical record (i.e., the patient associated with the context 402) as a clinical document. Such transcripts may also take the form of the preferred modality of the collaboration session, such as text messaging, voice, or other modalities as previously explained. Additionally, each transcript may be stored in a personal clinician record as a clinical document. Personal clinician records may be secure documents that can only be accessed by authorized users (e.g., may be password protected, etc.). Such personal clinician records are preferred when a collaboration session: (i) involves a general private conversation that is not to be accessed or reviewed by everyone who has authorized access to a given patient's record; or (ii) a specific private conversation based on the fact that the collaboration session spanned multiple patients and multiple pieces of context 402.

Once a transcript is embedded in or electronically attached to a patient record, it may be retrieved and viewed or played back in much the same way that a piece of patient-focused clinical data is chosen when initiating a request for a collaboration session. An example of a transcript may be the clinical document 506 displayed in the roster list shown in FIG. 5. In this way, the transcript itself may function as the context 402 about which the requesting clinician desires to have a communicative collaborative exchange with another clinician.

Therefore, the present invention can be seen to achieve increased efficiencies in the delivery of health care related services. These efficiencies are realized because, with the present invention, clinicians can more quickly and completely understand patient-focused clinical data in a respective electronic medical record by collaborating with other clinicians and software agents that have some level of specific knowledge and/or expertise to lend. Furthermore, since certain changes may be made in the above invention without departing from the scope hereof, it is intended that all matter contained in the above description or shown in the accompanying drawing be interpreted as illustrative and not in a limiting sense.

What is claimed is:

1. A method in a computer system having a processor and a memory the method comprising: receiving a request on a computer from a requesting clinician for a roster of potentially available clinicians and a collaboration session, the request initially includes at least one patient-focused clinical data element, wherein the at least one patient-focused clinical data element pertains to information contained within a patient's medical record;
    responsive to said request and said at least one patient-focused clinical data element, automatically determining by the computer, clinical content to be provided with at least one patient-focused clinical data element during the collaboration session, wherein the clinical content includes information contained within an electronic medical record associated with the patient;
    analyzing by the processor the request and the at least one patient-focused clinical data element to build a roster of potentially available clinicians based on the at least one patient-focused clinical data element, wherein the roster of potentially available clinicians includes one or more clinicians and one or more software agents, and wherein the one or more software agents are executable software program modules that are invoked for monitoring the collaboration session between at least two clinicians for triggering events, the triggering events causing the one or more software agents to perform clinically relevant tasks including clinically relevant data and delivering the clinically relevant data to the at least two clinicians during the collaboration session;
    acquiring presence information for each of the potentially available clinicians to be included in the roster of potentially available clinicians, said presences information indicating contact-type information, wherein the contact-type information includes dynamic information including one or more of the clinician's current location, online/offline status, current availability, and collaboration device capabilities;
    responsive to said at least one patient-focused clinical data element and said presence information, generating, by the processor, the roster comprising the one or more software agents, the potentially available clinicians and the corresponding presence information for each of the potentially available clinicians, wherein the presence information acquired is updated in real-time and displayed as part of the roster;
    receiving a selection from the requesting clinician regarding a preferred mode of electronic communication for the collaboration session, wherein the mode of electronic communication comprise real-time communicative collaboration capabilities; and
    facilitating the collaboration session between the requesting clinician and at least one of the potentially available clinicians on the roster, the collaboration session including a real-time communicative exchange utilizing electronic communication, wherein the step of facilitating the collaboration session includes inviting at least one of the potentially available clinicians on the roster.

2. The method of claim 1, wherein the at least one patient-focused clinical data element identifies at least one clinician within the patient's medical record.

3. The method of claim 2, wherein the step of analyzing the request includes determining the potentially available clinicians that practice with both the requesting clinician and the at least one clinician contained within the patient's medical record.

4. The method of claim 2, wherein the step of analyzing the request includes determining the potentially available clinicians related to the at least one clinician contained within the patient's medical record.

5. The method of claim 4, wherein the potentially available clinicians related to the at least one clinician contained within the patient's medical record are determined according to at least one of: clinicians within the same organization and clinicians sharing the same medical specialty.

6. The method of claim 1, wherein the patient-focused clinical data element includes information contained within the patient's medical record other than clinician information.

7. The method of claim 6, wherein the step of analyzing the request includes determining an author of the at least one patient-focused clinical data element.

8. The method of claim 7, wherein the step of analyzing the request further includes determining the potentially available clinicians related to the author of the at least one patient-focused clinical data element.

9. The method of claim 1, wherein the step of analyzing the request includes ranking the potentially available clinicians on the roster based on a clinical relevance scoring algorithm, wherein the scoring algorithm determines the degree of clinical relevance of each of the potentially available clinicians to at least one of the requesting clinician and the at least one patient-focused data element.

10. The method of claim 1, further comprising presenting the roster to the requesting clinician for modification.

11. The method of claim 1, wherein the electronic communication mode includes text messaging.

12. The method of claim 1, wherein the electronic communication mode includes voice over IP.

13. The method of claim 1, wherein the electronic communication mode includes video.

14. The method of claim 1, wherein the step of facilitating a collaboration session further includes inviting the one or more software agents based on at least one patient-focused clinical data element.

15. The method of claim 1, wherein the step of facilitating a collaboration session further includes receiving responses from the potentially available clinicians invited, the responses including electronic communication capabilities of each of the potentially available clinicians invited.

16. The method of claim 15, wherein the step of facilitating a collaboration session further includes establishing an appropriate connection for the collaboration session, the connection depending on the electronic communication capabilities of the requesting clinician and at least one of the potentially available clinicians invited that provided a response.

17. The method of claim 1, wherein the mode of electronic communication for the collaboration session is based on the capabilities of the requesting clinician and the roster of potentially available clinicians.

18. The method of claim 17, wherein the capabilities of the requesting clinician and the roster of potentially available clinicians include text messaging.

19. The method of claim 17, wherein the capabilities of the requesting clinician and the roster of potentially available clinicians include voice over IP.

20. The method of claim 17, wherein the capabilities of the requesting clinician and the roster of potentially available clinicians include video.

21. The method of claim 1, further comprising creating a transcript record of the collaboration session.

22. The method of claim 21, wherein the transcript record is stored within the patient's medical record as a clinical document.

23. The method of claim 21, wherein the transcript record is stored within a personal physician record as a clinical document.

24. The method of claim 21, further comprising retrieving and viewing of the transcript record of the collaboration session.

25. The method of claim 1, further comprising browsing the at least one patient-focused clinical data element by the requesting clinician and the at least one of the potentially available clinicians participating in the collaboration session.

26. The method of claim 25, wherein the browsing includes accessing a uniform resource locator (URL).

27. The method of claim 25, wherein the browsing includes accessing an application sharing mode.

28. The method of claim 1, wherein at least some of the potentially available clinicians on the roster share the same medical specialty, and wherein the step of facilitating a collaboration session includes: sending invitations to the potentially available clinicians on the roster to collaborate; receiving responses from the potentially available clinicians; and rescinding the invitations to the potentially available clinicians who share the same medical specialty when one of those clinicians having the same medical specialty accepts the invitation to collaborate.

\* \* \* \* \*